United States Patent
Pavlovic et al.

(10) Patent No.: US 11,890,262 B2
(45) Date of Patent: *Feb. 6, 2024

(54) NAIL HARDENING COMPOSITION AND METHOD OF USE

(71) Applicant: Wella Operations US, LLC, Calabasas, CA (US)

(72) Inventors: Elizabeta Pavlovic, Los Angeles, CA (US); Sunan Yuvavanich, Thousand Oaks, CA (US)

(73) Assignee: WELLA OPERATIONS US, LLC, Calabasas, CA (US)

( * ) Notice: Subject to any disclaimer, the term of this patent is extended or adjusted under 35 U.S.C. 154(b) by 624 days.

This patent is subject to a terminal disclaimer.

(21) Appl. No.: 16/629,377

(22) PCT Filed: Jul. 10, 2018

(86) PCT No.: PCT/US2018/041408
§ 371 (c)(1),
(2) Date: Jan. 8, 2020

(87) PCT Pub. No.: WO2019/014195
PCT Pub. Date: Jan. 17, 2019

(65) Prior Publication Data
US 2022/0211642 A1  Jul. 7, 2022

Related U.S. Application Data

(60) Provisional application No. 62/530,611, filed on Jul. 10, 2017.

(51) Int. Cl.
| | | |
|---|---|---|
| A61K 31/132 | (2006.01) | |
| A61P 17/02 | (2006.01) | |
| A61K 9/00 | (2006.01) | |
| A61K 9/06 | (2006.01) | |
| A61K 47/10 | (2017.01) | |
| A61K 47/12 | (2006.01) | |
| A61K 47/20 | (2006.01) | |
| A61K 47/38 | (2006.01) | |

(52) U.S. Cl.
CPC .......... *A61K 31/132* (2013.01); *A61K 9/0014* (2013.01); *A61K 9/06* (2013.01); *A61K 47/10* (2013.01); *A61K 47/12* (2013.01); *A61K 47/20* (2013.01); *A61K 47/38* (2013.01); *A61P 17/02* (2018.01)

(58) Field of Classification Search
CPC .................................................... A61K 31/132
See application file for complete search history.

(56) References Cited

U.S. PATENT DOCUMENTS

| | | | |
|---|---|---|---|
| 4,295,848 A | 10/1981 | Grollier et al. | |
| 5,628,991 A | 5/1997 | Samain et al. | |
| 9,017,704 B2 | 4/2015 | Blin et al. | |
| 11,628,148 B2* | 4/2023 | Pavlovic | A61K 47/38 514/673 |
| 2004/0067212 A1* | 4/2004 | Tokuyama | A61K 8/41 424/70.21 |
| 2008/0226573 A1 | 9/2008 | Schoon et al. | |
| 2012/0014892 A1 | 1/2012 | Renard et al. | |

FOREIGN PATENT DOCUMENTS

| | | | |
|---|---|---|---|
| DE | 2225541 A1 | 12/1973 | |
| DE | 102009017277 A1 * | 10/2010 | A61K 8/34 |
| EP | 0352375 A1 | 1/1990 | |
| EP | 3501489 A1 | 6/2019 | |
| WO | WO-9851265 A1 | 11/1998 | |
| WO | WO-2007148739 A1 | 12/2007 | |
| WO | WO-2019014195 A1 | 1/2019 | |

OTHER PUBLICATIONS

"International Application Serial No. PCT/US2018/041408, International Preliminary Report on Patentability dated Jan. 23, 2020", 10 pgs.

"Database WPI Week 200864", Thomson Scientific, London, GB; AN 2008-K94723 XP002784650, (Dec. 27, 2007), 5 pgs.

"International Application Serial No. PCT/US2018/041408, International Search Report dated Sep. 24, 2018", 5 pgs.

"International Application Serial No. PCT/US2018/041408, Written Opinion dated Sep. 24, 2018", 8 pgs.

* cited by examiner

*Primary Examiner* — John S Kenyon
(74) *Attorney, Agent, or Firm* — Dennemeyer & Associates LLC; Victoria Friedman

(57) ABSTRACT

A composition and method for treatment of brittle, broken, cracked or otherwise damaged nail and hoof plates. The composition is an aqueous-organic medium containing a non-covalent complex of a diamine and an organic acid or an aqueous-organic medium with a diamine alone.

25 Claims, No Drawings

NAIL HARDENING COMPOSITION AND METHOD OF USE

CLAIM OF PRIORITY

This patent application is a U.S. National Stage Filing under 35 U.S.C. 371 from International Application No. PCT/US2018/041408, filed on Jul. 10, 2018, and published as WO 2019/014195 on Jan. 17, 2019, which claims the benefit of priority to U.S. Provisional Application Ser. No. 62/530,611, filed Jul. 10, 2017, which are incorporated by reference herein in their entirety.

BACKGROUND

Human and animal digital soft tissue serves as one of the primary sensory interactions with a human or animal environment. For this reason, digital soft tissue is so sensitive to tactile, heat, cold and electromagnetic (infrared and UV light) radiation that too much can cause injury. The nail plates (or hooves) protect this digital tissue and the corresponding internal bone from assault and shock which would otherwise occur by heating, freezing, irradiating, touching, gripping, grasping, walking and/or standing with or on the digital appendages. For example, human finger nails absorb and repel shock to the soft tissue and bone when the end of a finger is slammed against a hard object. A nail plate that is weak, brittle, cracked and/or broken does not protect against this shock so that the assault results in significant pain.

Traditionally, broken, cracked or weak nail and hoof plates have been treated with a formaldehyde composition to mend the breaks and cracks. The formaldehyde reacts with the proteins of the nail or hoof to form imine bonds and harden the tissue. Not only does the treatment include strong odor but also kills associated cells and causes allergic reaction. The treatment is the same as is performed by embalming techniques.

Nevertheless, formaldehyde treatment of cracked and broken nails and hooves is the currently approved FDA treatment. Recently, other aldehyde formulations have been developed in attempts to circumvent the undesirable side effects of formaldehyde treatment. Citral, lemonal/geranial and citronellal are aldehydic terpenoids traditionally used in minute amounts for aroma development in perfumes. Recently, citral and citronellal formulations having higher concentrations of this aldehyde have been developed for use in nail hardening applications. The difficulties associated with formaldehyde also plaque these longer carbon chain aldehydes.

Other nail hardening treatments include iodine, hydrazines, divinyl sulfone and dithiopyridine. Of these, iodine is the active ingredient in some commercial nail strengtheners while hydrazines, divinyl sulfone and dithiopyridine are not regarded as safe alternatives to formaldehyde. Bismaleimidohexane and bismaleimidotriethylene glycol are also agents known for treatment of brittle, frizzy hair. They might also be useful as well for hardening of nails since nails and hair include similar families of proteins.

Therefore, it is desirable to develop a safe, effective, non-offensive treatment for weak, broken, cracked nail plates and hooves. An additional goal includes development of formulations that effectively treat weak, broken, cracked nail plate without inclusion of concentrated ingredients. Another goal includes the development of a formulation that does not cause discoloration of a human nail plate and that can optionally be combined with color components for coloring a nail plate.

SUMMARY OF THE INVENTION

The present invention is directed to a composition and a method for hardening of a nail or hoof that is weak, brittle, inflexible, cracked and/or broken. The composition includes as a first embodiment a diamine alone in an aqueous/organic solvent medium. The composition includes as a second embodiment a non-covalent complex of a diamine and an organic acid at a molar ratio range of 1:1 to 1:4, preferably 1:2 in an aqueous/organic solvent medium. The diamine is an alkylenyl or aromatic diamine. The organic acid is a saturated or unsaturated (olefinic) mono or di carboxylic, phosphoric or sulfonic acid. Preferred are unsaturated mono or di carboxylic acids. The aqueous/organic solvent medium may be a mixture of water and alcohol such as $C_1$ to $C_6$ mono alcohol or a combination of the monoalcohol and a polyol such as glycerin, propylene glycol, polyethylene glycol of 2 to 6 glycol units or polypropylene glycol of 2 to 6 glycol units. Additional, optional components of these compositional embodiments include one or more film formers, one or more activatable polymers, one or more surfactants, one or more plasticizers, one or more fatty alcohols, one or more rheologic control agents, one or more nail penetrating agents, one or more perfumes, one or more color agents and any combination thereof.

Embodiments of the method include application to a clean, dry nail plate or hoof of a flowable formulation of one of the compositional embodiments at a concentration of the complex in aqueous/organic solvent medium at from about 1 wt % to about 8 wt %, preferably about 2 wt % to about 5 wt %, more preferably about 2 wt % to about 4 wt %, most preferably about 3 wt % relative to the total weight of the composition. The applied coating is allowed to remain in at least semifluid state on the nail plate for a period of 2 to 40 minutes, preferably a period of 5 to 15 minutes. The nail plate is optionally recoated with the flowable coating and after a period of 10 minutes to one hour, the coating is air dried with optional application of mild heat. The semi fluid state of the coating is preferably accomplished by inclusion of a rheologic control agent in the aqueous/organic solvent medium.

DETAILED DESCRIPTION OF THE INVENTION

The present invention provides a composition and method for a treatment of a painful, difficult to heal condition of human nail plates and animal hooves. Weak, brittle and/or inflexible nails and hooves are susceptible of cracking, breaking, fracturing and/or splitting down to soft tissue nail and hoof beds. When this happens, the person or animal suffers pain that at times is unbearable. Treatment according to the present invention alleviates the pain and helps the nail plate or hoof heal.

Definitions

Unless defined otherwise, all technical and scientific terms used herein have the same meaning as commonly understood by a person of ordinary skill in the art.

As used herein and in the appended claims, the singular forms "a," "an" and "the" include plural referents unless the context clearly dictates otherwise.

The term "about" as used herein, when referring to a numerical value or range, allows for a degree of variability in the value or range, for example, within 10%, or within 5% of a stated value or of a stated limit of a range.

All percent compositions are given as weight-percentages relative to the total weight of the composition, unless otherwise stated.

All average molecular weights of polymers are weight-average molecular weights, unless otherwise specified.

The term "may" in the present context means "is permitted to" or "is able to" and is a synonym for the term "can." The term "may" as used herein does not mean possibility or chance.

The term "and/or" means both or all of the items together to which these conjunctions refer and well as each of the items alone and separate from the others. When more than two items are referred, the term and/or also means any combination of these multiple items as well as all and each.

The term "substantially free" as the term is used herein means completely or almost completely; for example, a composition that is "substantially free" of a component either has none of the component or contains such a small amount that any relevant functional property of the composition is unaffected by the presence of the small amount of the component in question. A compound that is "substantially pure" has only negligible traces of impurities present.

The term "substantial" means a significant amount such as more than a majority amount. For example, a mixture of compounds A and B in which A is present in a substantial amount means that A is present at a weight percent or number of moles that is greater than the weight percent or number of moles of B. This term also means more than a minimal characteristic, examples of which include substantial flow or substantial color or substantial treatment.

The following groups of terms are used throughout this application: 1) preferred, preferably and preferable; 2) more preferred, more preferably and more preferable, 3) especially more preferred, especially more preferably and especially more preferable; 4) most preferred, most preferably and most preferably; 5) especially most preferred, especially most preferably and especially most preferable; and 6) very especially most preferred, very especially most preferably and very especially most preferable. These groups convey a meaning of preference for a group of substituents, structures, moieties, components and compounds. The degree of preference is self-explanatory by the terms themselves. Within each group, the meanings of the synonyms, preferred, preferably and preferable are the same. There is no difference in meaning in the context of this application when a group is described in a particular sentence as preferred and then in another sentence this same group is described as preferably. Not all six categories of preference are used in this application to describe each and every substituent, formula, subgenus integer symbol and atom designator. In some instances, two or three categories are used while in other categories five or six categories are used. The degree of preference as expressed by these terms for members of series which progress from many to a few individually named components is self-explanatory and internally consistent for the particular series being described.

The term diamine means a linear alkylene or aromatic diamine having from 2 to 12 carbons in the alkylene group and 6 or 10 carbons in the aromatic group. The alkylene group is —$(CH_2)_n$— wherein n is an integer of 2 to 12. The aromatic group is phenyl or naphthyl. The termini of the alkylene group and the aromatic group are primary amines: —$NH_2$.

The term organic acid means a $C_2$ to $C_{10}$ organic mono or di-carboxylic, phosphoric or sulfonic acid that has an olefinic in the organic moiety. An exemplary olefinic acid is an alkenyl carboxylic, phosphoric or sulfonic acid having two to ten carbons in the alkenyl group.

The term film former means a fully formed polymer such as a poly(meth)acrylate, polyester, polyamide, polyurethane, cellulosic ether or ester or shellac that will form a contiguous film or layer when the film former in an organic or aqueous medium is coated on a substrate and dried to remove the medium. The film former does not undergo cross-linking or other chemical reaction after its deposition as a film.

The term activatable polymer means a polymer, oligomer or monomer that can be polymerized and/or crosslinked by actinic radiation or chemical cross-linking reaction following its deposition as a gel coating or layer.

The term surfactant means a zwitterionic, nonionic, anionic or cationic compound having lipophilic and hydrophilic qualities so that it can function to solubilize lipophilic substances in hydrophilic and/or aqueous media.

The term plasticizer means a compound that is compatible with a film former and/or an activatable polymer and provides additional flexibility and elasticity to the film former and/or activatable polymer when present as a solid layer, coating or material.

The term rheologic control agent means a rheology modifier that will thicken an otherwise free-flowing liquid composition. The modification renders the composition flowable when applied by spray, brush or other coating method but the composition will remain in a static position in a quiescent state. These agents are typically classed as thixotropic agents. Examples include polyvinyl alcohol, a polyethylene glycol, vegetable gum and hydrocarbon wax.

The term alcohol means a mono, di or polyol that can solubilize other components of the composition. Alcohols include ethanol, propanol, butanol, pentanol, hexanol, glycol, glycerin (glycerol), propylene diol, hexane diol, octane diol or polyethylene or polypropylene glycol.

The term coloring agent includes a red, green, blue, yellow orange, pink, brown or black pigment that will form a colored layer in combination with a film former and/or an activatable polymer.

The term penetration agent means an organic compound that facilitates penetration of organic solids through the dermis and/or corneum layers of nail plates. Examples include dimethyl sulfoxide, lauryl sulfate, dimethyl formamide, glycerol and azone.

The term gel means a liquid within a three-dimensional network that ensnares the liquid and forms a solid-like consistency in the static, quiescent state. The gel has sufficient rheologic control and/or density at rest (static state) to maintain continuous integrity of the liquid gel as a coating or layer on a flat or curved surface. The gel character of the liquid means that the liquid will not spontaneously flow off a surface on which it has been coated but can be readily removed by mechanical force such as by wiping with a cloth or tissue.

The term flowable means a liquid that will flow like water or an aqueous latex paint when contacted by mechanical means such as by a brush, sponge or other applicator.

Together, the terms gel and flowable mean that the liquid having these characteristics is thixotropic.

The term alkylenyl means a linear hydrocarbon chain with open valences at both termini. An example is hexylenyl of the formula —$(CH_2)_6$—.

Components of the Composition

Certain aspects of the invention enable healing of broken, cracked, weak, brittle, inflexible or otherwise injured nail plate or hoof plate. These aspects are achieved at least in part by the compositional embodiments of the invention. These embodiments include a first compositional embodiment of a diamine alone in an aqueous-organic medium and a second compositional embodiment of a noncovalent complex of a diamine and an organic acid in an aqueous-organic medium. The diamine alone or as a component of the complex rebinds broken proteins thereby providing flexibility and ameliorating brittleness, cracked, broken and/or weak nail plates. The acid component of the complex lessens the yellowing effect that diamine otherwise has upon a nail plate. It has been found that the non-covalent complex rather than a corresponding covalently bonded complex is an aspect of the second composition embodiment of the invention.

Optional components of the composition include a film former, an activatable polymer, a surfactant, a plasticizer, a fatty alcohol, a rheologic control agent, a penetrating agent, a perfume, a coloring agent and a preservative. Any and all combinations of these optional components may be included in the composition.

The composition includes an aqueous-organic solvent medium that optionally contains a rheologic control agent to assure flowability when applying the composition but also assuring coating integrity of the composition in a static state. The rheologic control agent maintains suitable coating density (viscosity) on a substrate so that the coating in a semi-fluid but static state can effectively penetrate the surface of the nail plate. Preferably, this characteristic is present because the composition preferably has thixotropic properties. Alternatively, the aqueous-organic composition does not include a rheologic control agent. In this embodiment, the nail plate or hoof is immersed in the free-flowing liquid composition.

To promote the healing properties of the composition when a nail plate cannot be immersed in the composition, a coating of the composition on the nail plate is kept in place as a gel through inclusion of the rheologic control agent. The gel composition contacts the nail plate for sufficient time to allow the complex to penetrate the surface of the plate into the internal region of the plate. Penetration allows contact of the complex with broken peptide bonds of the internal regions of the plate and the underlying nail bed. The rheologic control of the composition lessens or prevents spontaneous flow of the composition once the composition is coated onto the nail plate. While the rheologic control agent enables the composition to form a contiguous flowable coating over the nail plate when applied, the rheologic agent also enables the coating to maintain its integrity and remain in place once the coating has covered the nail plate. This characteristic allows the gel coating to maintain contact with the nail plate for a sufficient time to enable penetration of the complex into the internal region of the nail plate.

In the alternative, the composition is formulated as a free-flowing liquid in an aqueous-organic medium without a rheologic control agent and the nail or hoof plate is immersed in the liquid composition for a sufficient time to allow penetration of the complex through the surface of the plate and into its internal region.

The first embodiment of the composition includes the diamine alone in the medium and can include all other compositional components described herein. The diamine alone is preferably maintained at a pH that promotes nail plate penetration as described below. The second embodiment of the composition includes the non-covalent complex of the diamine and organic acid. The complex has a molar ratio of diamine to organic acid of about 1:1 to about 1:4, preferably about 1:1.5 to about 1:4, more preferably about 1:1.5 to about 1:3 and most preferably about 1:2. The complex in a preferred form is an ionic complex between the diamine and organic acid.

While not a limitation of the invention, it is believed that the acidity or neutrality of the composition and the nail or hoof plate medium promote complex penetration of the plate and subsequent plate protein-complex interaction. The pH of the medium and the nail plate at least in part is believed to manage this aspect. The nail plate is slightly acidic with a pH of about 5.3 and is negatively charged due to the protein constituents of the nail or hoof plate. Although it is not a limitation of the invention, it is believed that the neutral form (unprotonated form) of the diamine facilitates its diffusion into the nail or hoof plate and subsequent interaction with plate proteins. It is theorized that acidic pH of the nail or hoof plate protonates the neutral diamine at least in part and the negative charge of the plate draws in the resulting, positively charged diamine. While the pH of the composition may range from moderately acidic to moderately basic, preference is toward slightly acidic to neutral. If no pH control agent is included, the pH is established by the pKb of the amine alone or the respective pK's of the organic acid and the diamine and subsequently by pH of the nail or hoof plate. Depending on the molar ratios used, the pH of the composition can range from about slightly acidic to slightly basic or from about a pH of 6 to about 8, preferably about 7. Penetration of the amine alone or the complex is believed to be helped when the pH is in an approximate neutral range of about 6.8 to about 7.2. Protein binding by the amine alone or the complex is also believed to be managed under appropriate pH conditions of slightly acidic to neutral. The pH can also be managed by addition of buffers and pH modifiers such as hydrochloric acid, sodium hydroxide, sodium carbonate/bicarbonate and/or acetic acid/sodium acetate. This management typically will maintain an approximate neutral pH for the composition.

The diamine is an alkylenyl or aromatic diamine. The alkylenyl diamine has Formula I with n as an integer of 2 to 12:

$$H_2N-(CH_2)_n-NH_2 \qquad \text{Formula I.}$$

Exemplary diamines are α,ω alkylenyl diamines such as diaminopropane, diaminobutane, diaminopentane, diaminohexane, diaminoheptane, diaminooctane, diaminononane, diaminodecane, diaminoundecane or diaminododecane. The aromatic diamine is either 1,2-diaminobenzene or 1,8 diaminonaphthalene.

The organic acid is itaconic acid or a mono or di carboxylic (—COOH), phosphoric (—OPO(OH)$_2$) or sulfonic (—SO$_2$OH) with an unsaturated aliphatic group of Formula II:

$$R^1-CY-Z-CH-R^2-X \qquad \text{Formula II.}$$

The substituent designators of Formula II include $R^1$, $R^2$, X, Y and Z. Z designates an unsaturated bond between CY and CH. With Z as an unsaturated group, the moiety —CY—Z—CH— is —CY=CH—. $R^1$ is phenyl or an alkyl group of one to four carbons. $R^2$ is an optional alkylenyl group of the formula —(CH$_2$)$_m$— wherein the designator m is zero or an integer of 1 to 4 such that $R^2$ is either absent or is present as a carbon chain. Y and X are each independently hydrogen or a carboxylic, phosphoric or sulfonic acid group provided that at least one of X and Y is an acid group.

The unsaturated diacids of Formula II are preferred. The unsaturated organic acids of Formula II are preferred and of these, the unsaturated or olefinic diacids of Formula II are preferred. More preferred olefinic acids are the alkenyl dicarboxylic, diphosphoric or disulfonic acids having two to ten carbons in the alkenyl group. Further preferred olefinic acids include those having an α,β unsaturation. Exemplary organic unsaturated acids include cinnamic acid, (meth) acrylic acid wherein the phrase (meth) means either or both of acrylic acid and methacrylic acid, butenoic acid, pentenoic acid and olefinic diacids including maleic acid, fumaric acid, itaconic acid, butenyl-1,4-dicarboxylic acid, hexenyl-1,6-dicarboxylic acid, butenyl-1,4-diphosphoric or disulfonic acid, hexenyl-1,6-disulfonic or diphosphoric acid, vinyl-1,2-diphosphoric or sulfonic acid, and pentenyldicarboxylic acid. While the anhydrides and amides are also included, the acids are preferred. Especially preferred olefinic acids include maleic acid, fumaric acid, itaconic acid, and (meth) acrylic acid.

The liquid medium of the composition is an aqueous-organic liquid mixture with a majority concentration of organic solvent. The organic solvent may be an alcohol, a ketone or a water-soluble terpenoid or any mixture or combination thereof.

The alcohol may be a mono, di or polyalcohol or may be a mixture of such alcohols. Preferably, the alcohol component is a mixture of a monoalcohol such as ethanol or propanol and a combination of polyols such as glycerol and polyethylene glycol 10-100 or polypropylene glycol 10-100. The number designations with the PEG and PPG indicate the number of glycol units in the PEG or PPG. Any mixture of any combination of the mono, di and/or polyalcohols may be employed.

The ketone is water soluble and may be acetone, methyl ethyl ketone (i.e., butanone), pentanone, hexanone or a mixture thereof. One or more of the ketones can be combined with one or more alcohols described above to form the organic portion of the aqueous-organic medium.

The terpenoid is a water-soluble hydrocarbon derivative based upon isoprene units and also having hydroxyl and/or carboxyl groups to provide water solubility. Examples include citral, menthol, camphor and hydroxyl limonene and mixtures thereof.

One or more of the water soluble terpenoids can be combined with one or more of the ketones and alcohols described above to form the organic portion of the aqueous-organic medium. In some instances, the water soluble terpenoid also may act as a surfactant and as a plate penetrating agent.

The film former of the composition is a fully formed non-cross linkable polymer. The film former (non-cross-linked polymer) may be a poly(meth)acrylate, a polyester, a polyamide, a polyurethane, a cellulosic ether or ester or a shellac that will form a contiguous film or layer when the film former in an organic and/or aqueous medium is coated on a substrate and dried to remove the medium. The polyester may be a polymer of an hydroxycarboxylic acid or a polymer of a diol and dicarboxylic acid. The polyamide may be a polymer of an amino carboxylic acid or a diamine and a diacid. The polyurethane is a polymer of a diol and a diisocyanate.

Exemplary film formers include poly methyl or ethyl (meth)acrylate, a copolymer of methyl or ethyl (meth) acrylate and styrene or vinyl methoxide, a styrene/acrylate/ ammonium acrylate copolymer, a vinyl copolymer such as polyvinyl butyral or polyvinyl chloride, polylactide, polyglycolide, a copolymer of lactide and glycolide, polyester of C4-C6 alkylene diol and C4-C6 alkylenyl dicarboxylic acid, adipic acid/neopentyl glycol/trimellitic anhydride copolymer, polyamide of C4-C6 alkylene diamine and C4-C6 alkylenyl dicarboxylic acid, a polyurethane of C4-C6 alkylenyl diol and C4-C6 alkylenyl diisocyanate or 1,4-diisocyanatobenzene, methyl, ethyl, and/or propyl cellulose, cellulose acetate, cellulose propionate, nitrocellulose, cellulose acetate butyrate, cellulose butyrate, hydroxyethyl cellulose, hydroxypropyl cellulose, carboxymethyl cellulose, hydroxypropyl methyl cellulose and similar cellulose esters and ethers.

As film former polymers, the poly(meth)acrylate, polyester, polyamide, polyurethane and cellulosic ether or ester do not contain side chains or terminal groups that would render the polymer susceptible of cross linking. Polymers with such side chains and/or terminal groups are described below as activatable polymers.

The activatable polymer is a monomer, oligomer or polymer of monomeric units like those of the film formers described above and in addition have side chains and/or termini that can be cross-linked by formation of carbon-carbon bonds through vinyl groups, formation of ester bonds by combination of hydroxyl and acid groups, formation of amide bonds by combination of amine and acid groups or formation of urethane bonds by combination of hydroxyl and isocyanate groups. In each instance, the side chain or terminus of the monomer, oligomer or polymer will have one of the members of these bonds and a linker molecule will have two of the other member of the bond. For example, if the side chain or terminus is a vinyl group such as a (meth)acrylate joined to the polymer or oligomer by ester formation, the linker will be a divinyl compound such as propylenyl-1,3-bis(meth)acrylate or divinyl benzene. If the side chain or terminus is a hydroxyl group, the linker will be a diacid or a diisocyanate. A specific example includes a copolymer of methyl (meth)acrylate and hydroxymethyl (meth)acrylate which can be cross linked with phthalic acid, a C2-C6 alkylenyl dicarboxylic acid or diisocyanatobenzene or cyclohexane diisocyanate. Another specific example is a polyurethane having terminal hydroxyl groups that is esterified with (meth)acrylic acid to form polyurethanyl bis(meth) acrylic ester. This polymer can be cross linked with divinyl benzene.

Additional exemplary activatable polymers include (meth)acrylate polymers and oligomers having hydroxyalkyl groups among the esterifying moieties of the acrylate ester groups. The hydroxyalkyl groups can be cross linked with diisocyanate cross linkers, or with diacids. Another crosslinkable polymer is a polyester formed with a diol and a molar excess of a diacid to form an oligomer (short chain pre-polymer) followed by additional polyester formation using a triol. The triol provides a third pendant side chain hydroxyl group that can be cross linked using additional activated diacid.

Surfactants are surface-active agents that can reduce the surface tension of water and enable water insoluble components to be included in the aqueous-organic medium. The surfactants may be non-ionic, amphoteric, anionic, or cationic. More than one surfactant may be included in the formulation. The non-ionic, anionic, cationic and amphoteric surfactants are well-known in the cosmetics industry. See for example "Surfactants in Personal Care Products and Decorative Cosmetics", $3^{rd}$ Ed. By L. Rhein, M Schlossman, A O'Lenick and P Somasundaran, CRC Press, 2006. This text provides some exemplary surfactants that may be used in the present composition, the disclosure of which is incorporated herein by reference.

Suitable anionic surfactants include those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate.

Exemplary cationic surfactants include quaternary ammonium compounds such as benzalkonium chloride, benzethonium chloride, cetrimonium bromide, stearyl dimethylbenzyl ammonium chloride, polyoxyethylene/coconut amine, behenalkonium chloride and behentrimonium chloride.

Examples of nonionic surfactants include sucrose acetate/isobutyrate, ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, polyoxyethylene hydrogenated tallow amide, a polyoxyether of lauryl alcohol or ceteareth-20 and/or combinations thereof.

Examples of amphoteric surfactants include sodium N-dodecyl-β-alanine, sodium N-lauryl-β-iminodipropionate, myristoamphoacetate, lauryl betaine and lauryl sulfobetaine.

The plasticizer provides flexibility to a film former or an activatable polymer. Plasticizers include di and tri esters of moderate molecular weight such as trimethyl pentanyl diisobutyrate or acetyl tributylcitrate or acetyl tripropyl ascorbate or dihexyl succinate.

The rheologic agent controls the viscosity of the composition so that preferably it is flowable under pressure and is gel like in a steady state (rest). The thixotropic property is attendant with the activatable polymers and the film formers as well as with clays, starches, gums and derivatives thereof. While the activatable polymers and film formers are optional components of the present composition, clays, starches, gums and their derivatives are not. Clays, starches, gums and their derivatives would not facilitate the treatment aspect of the composition. Another rheologic agent useful for the present composition is a polyol of moderate to molecular weight. Polyglycols, polyethers, polyols and polyesters with moderate to high intrinsic viscosities will contribute the rheologic control for accomplishment of the above described flowable/gel properties of the present composition. Exemplary components include polyethylene and polypropylene glycols of about 50 to about 10,000 or higher units, polyethers of butylene oxide and/or pentylene oxide having about 20 to more than 10,000 or higher units, Polyesters such as polylactide, polyglycolide and copolymers thereof as well as block copolymers of such polyesters and polyethylene and/or polypropylene glycol also serve as useful rheologic control agents of the present composition. Preferably, rheology control provides thixotropic properties to the composition so that it will flow under force of spraying, brushing or otherwise applying but in a static state, the composition is viscous enough to prevent flow.

The fatty alcohol serves as an emulsifying agent and/or an anti-agglomeration and/or smoothing agent to promote substantially uniform flow of the composition as it is applied to a nail or hoof plate. The fatty alcohol may be a C8 to a C36 linear or slightly branched alkyl monoalcohol or may alternatively be a fatty alcohol of this configuration covalently bound as an ether to a polyethylene glycol or polypropylene glycol having 5 to 20 glycol groups.

The penetrating agent facilitates transport or carry of other agents through the plate surface into the interior of the plate. These agents are known and include dimethyl sulfoxide (DMSO), dimethyl formamide (DMF), lauryl sulfate, glycerin, dodecylazacycloheptan-2-one (azone), N-methyl pyrrolidone, di and tetra ethylene glycol, lauric, myristic or capric acid, and terpenoids.

Perfumes such as cinnamon, cascarilla, safrole, rose, jasmine, *mimosa, narcissus*, cassie, citrus, apple, strawberry, cherry, lavender, patchouli, sage, violet, rosemary, myrrh, benzoin, pine, fir amber, copal, and related odoriferous esters and terpenes are useful as optional components in the present composition.

Preservatives such as alkyl parabens, phenoxyethanol, benzoic acid, germaben, DMDM hydantoin, diazolidinyl urea are useful as optional components in the present composition.

Coloring agents including enamels, pigments and metal oxides are useful as optional components in the present composition.

Compositional Ratios and Concentrations

Embodiments of the present composition include as a basis, the aqueous-organic medium and either the diamine alone or the diamine-organic acid complex. For the compositional embodiment containing the complex, the molar ratio of diamine to acid of the complex ranges from about 1:1 to about 1:4, preferably about 1:1.5 to about 1:4, more preferably about 1:1.5 to about 1:3 and most preferably about 1:2. If the acid is a diacid, the most preferable ratio is about 1:2. If the acid is a monoacid, the ratio is about 1:2 to about 1:3.

The diamine alone or as a component of the complex promotes treatment of the affected nail plate. While the use of the diamine alone may cause yellowing of the nail plate, its concentration in the composition can be adjusted to minimize or eliminate the yellowing. As the complex, the acid component eliminates or at least ameliorates the yellowing tendency. The yellowing effect is believed to be the result of Schiff base formation between the diamine and carbonyl groups of the keratin protein of the nail bed.

The concentration of the diamine alone or the complex in the aqueous-organic medium ranges from about 1 wt percent to about 8 wt percent, preferably about 1 wt percent to about 7 wt percent, more preferably about 1 wt percent to about 5 wt percent, especially more preferably about 1 wt percent to about 3 wt percent, most preferably about 3 wt percent. The weight percentages are relative to the total weight of the composition including any optional components.

The aqueous-organic medium is a mixture of water and one or more organic solvents. On a weight percentage basis, the total concentration of organic solvent ranges from about 30 wt percent to about 95 wt percent relative to the total weight of the medium (not the total composition). Preferably, the total organic solvent concentration ranges from about 50 wt percent to about 95 wt percent, more preferably about 65 wt percent to about 90 wt percent, most preferably about 75 wt percent to about 85 to 90 wt percent relative to the total weight of the medium, not the composition.

The kinds of organic solvents range from monoalcohols to polyols to ketones to terpenoids. The major portion of solvent may be monoalcohols. A significant but less than major portion of solvent may be polyols. A less significant portion of solvent may be ketones. A minor portion of the solvent may be terpenoids. The concentration of mono alcohols may range from about 40 to about 90 weight percent of the total amount of organic solvent, preferably about 50 to 80 weight percent of the total amount of organic solvent, more preferably about 50 to about 70 weight percent of the total amount of organic solvent. The concentration of polyols including PEG and/or PPG ranges from about 10 weight percent to about 60 wt percent, preferably about 15 weight percent to about 50 weight percent, more preferably about 15 weight percent to about 40 weight percent, most preferably about 20 weight percent to about 35 weight percent relative to the total amount of organic solvent. The concentration of ketones ranges from about 2 weight percent to about 20 weight percent, preferably about 2 weight percent to about 15 weight percent, more preferably about 2 weight percent to about 10 weight percent relative to the total weight of the organic solvent. The concentration of terpenoid ranges from 0.1 weight percent to about 5 weight percent, preferably about 0.5 weight percent to about 3 weight percent, more preferably about 0.5 weight percent to about 1.5 weight percent relative to the total weight of the organic solvent.

In addition to mixtures, the organic solvent may be a single or a mixture of monoalcohols, a mixture of one or more monoalcohols and one or more polyols alone at the weight percentages given above, a mixture of one or more monoalcohols and one or more ketones at the weight percentages given above. Terpenoids are optional in all circumstances.

The remaining components described above are optional additives to the present composition.

The film former alone, the activatable polymer alone or a mixture thereof may range in concentration relative to the total weight of the composition from about 1 weight percent to about 40 weight percent, preferably about 1 weight percent to about 30 weight percent, more preferably about 3 weight percent to about 20 weight percent, most preferably about 3 weight percent to about 15 weight percent. When a combination of the film former and activatable polymer is included in the present composition, the weight percentage of film former relative to the total weight of the combination (not the composition) ranges from about 50 weight percent to about 99 weight percent with the remainder being activatable polymer, preferably from about 60 weight percent to about 90 weight percent, more preferably from about 60 weight percent to about 80 weight percent, most preferably from about 70 weight percent to about 80 weight percent.

The concentration of surfactant may range from about 2 weight percent to about 15 weight percent relative to the total weight of the composition, preferably about 2 weight percent to about 10 weight percent, more preferably about 2 weight percent to about 6 weight percent, most preferably about 2 weight percent to about 4 weight percent.

The concentration of plasticizer may range from about 0.1 wt percent to about 5 wt percent relative to the total weight of the composition, preferably about 0.1 wt percent to about 3 wt percent, more preferably about 0.1 wt percent to about 1 wt percent, most preferably about 0.2 wt percent to about 0.6 wt percent.

The concentration of fatty alcohol may range from about 2 weight percent to about 15 weight percent relative to the total weight of the composition, preferably about 2 weight percent to about 10 weight percent, more preferably about 2 weight percent to about 6 weight percent, most preferably about 2 weight percent to about 4 weight percent.

The concentration of rheologic control agent may range from about 2 weight percent to about 15 weight percent relative to the total weight of the composition, preferably about 2 weight percent to about 10 weight percent, more preferably about 2 weight percent to about 6 weight percent, most preferably about 2 weight percent to about 4 weight percent.

The concentration of penetration agent may range from about 1 weight percent to about 8 weight percent relative to the total weight of the composition, preferably about 1 weight percent to about 5 weight percent, more preferably about 1 weight percent to about 3 weight percent, most preferably about 1 weight percent to about 2 weight percent.

The concentration of each of the perfume and coloring agent may range from about 0.1 weight percent to about 5 weight percent relative to the total weight of the composition, preferably about 0.1 weight percent to about 3 weight percent, more preferably about 0.1 weight percent to about 2 weight percent, most preferably about 0.1 weight percent to about 1 weight percent.

The preservative may range from about 0.1 weight percent to about 2 weight percent relative to the total weight of the composition, preferably about 0.1 weight percent to about 1.5 weight percent, more preferably about 0.1 weight percent to about 1 weight percent, most preferably about 0.1 weight percent to about 0.5 weight percent.

Methods

Exemplary methods of the present invention involve application of the formulated composition to the nail or hoof plate for a sufficient time to enable penetration of the diamine alone or the complex through the plate surface and into the interior of the plate. Penetration also preferably delivers the complex to the interface between the nail or hoof plate and bed.

While a combination of aqueous-organic medium and diamine alone or complex alone can enable this delivery to the interior of the plate and to the interface, the delivery is facilitated by penetration agents, by surfactants, by fatty alcohols and by plasticizers. Any or all or any combination of these components can be employed to promote delivery.

The embodiments of the method include immersion and/or coating. In the immersion method, the nail plate or hoof is immersed in a free-flowing composition for a sufficient time to enable delivery of the diamine alone or the complex to the interior of the plate or hoof and to the interface. In the coating method, the nail or hoof plate is coated with the composition by painting, brushing sponging, spraying or otherwise applying the coating to the plate. The composition in this instance is preferably formulated to be a flowable gel so that it will substantially uniformly produce a contiguous, complete coating on the plate when applied but will be statically stationary following application so that it will not flow off the plate.

For immersion and for coating, the composition wet with the aqueous-organic medium is allowed to remain in contact with the plate for a time sufficient to permit penetration of the complex into the interior of the plate and to preferably contact the nail or hoof bed. Typical times for contact range from 2 minutes to multiple hours. In severely damaged nails and/or hooves, the contact time will be long so that penetration will be thorough. Typical contact time for damaged human finger nails will range from 1 minute to 1 hour, preferably 1 minute to 30 minutes, more preferably 1 minute to 15 minutes, most preferably about 1 minute to about 5 minutes.

After a sufficient time for contact and penetration is accomplished, the "wet" composition can be dried by air dry techniques optionally using moderate forced air such as from a hair drier or heated air gun. If a film former is present, the drying activity will establish a film or dry coating of the film former on the surface of the nail or hoof. Depending on the concentration of the film former in the "wet" composition, the cross-sectional dimension of the dry film will range from about 0.01 millimeters to about 1 millimeter, preferably about 0.01 millimeter to about 0.5 millimeter. Higher concentrations of film former will produce thicker dry films which can be accomplished if desired. However, thick films on a nail or hoof may not be desirable and may tend to flake.

If an activatable polymer is present in the composition alone or in combination with the film former, the foregoing drying technique can also be employed along with the appropriate activity for obtaining cross linking of the activatable polymer. If the cross linking is to be accomplished by a chemical reaction such as by formation of ester, amide, or urethane bonds, the cross linker in the same aqueous-organic medium used for the complex with activatable polymer is applied just prior to drying. The drying by moderate heat will activate the chemical cross linking. The cross-linking reaction will preferably generate sufficient heat to complete the drying stage. If not, external moderate heat can continue to be applied.

Following the drying/cross-linking, a contiguous, uniform coating of the cross-linked polymer on the nail or hoof plate is formed. Its cross-sectional dimension preference is the same as that described above for the film former.

The coating can be removed from the nail or hoof plate after a sufficient time has passed to allow the nail bed to reform a contiguous, natural nail or hoof plate. In some instances, the coating will naturally wear away as the nail or hoof plate regrows. If early removal is desired, the coating can be eliminated by solvent and abrasion. Film former coatings can be removed by solvent elimination. Cross linked polymer coatings are tougher and are therefore desirable in situations where that nail or hoof is subjected to stress or mechanical attack. Inclusion of a film former in the activatable polymer can provide for an easier solvent removal of the cross-linked polymer nail or hoof film.

Exemplary Compositions

Exemplary compositions for application to nail or hoof plate are formulated for application by brush, spray or sponge onto the plate.

Composition 1
  Components and Concentrations
  a) 1,6 diamino hexane and maleic acid at a 1:2 molar ratio, 3 wt % concentration;
  b) Ethanol—60 wt %;
  c) Water—17 wt %;
  d) PEG 100-5 wt %;
  e) Nitrocellulose—7 wt %;
  f) Stearyl alcohol—4 wt %;
  g) Behentrimodium chloride—1 wt %;
  h) DMSO—3 wt %.
  Concentrations are in weight percentage relative to the total weight of the composition.

Composition 2
  Components and Concentrations
  a) 1,5 diamino pentane and methacrylic acid at a 1:4 molar ratio, 3 wt % concentration;
  b) Propyl alcohol—50 wt %;
  c) Water—20 wt %;
  d) PPG—3 wt %;
  e) Ethyl cellulose—10 wt %;
  f) Cetyl alcohol—5 wt %;
  g) Cetyl trimethyl ammonium chloride;
  h) DMSO—5 wt %.
  Concentrations are in weight percentage relative to the total weight of the composition.

Composition 3
  Components and Concentrations
  a) 1,6 diamino hexane and itaconic acid at a 1:2 molar ratio, 3 wt %;
  b) Ethyl alcohol—80 wt %;
  c) Water—10 wt %;
  d) Cellulose acetate—5 wt %;
  e) DMSO 5 wt %.
  Concentrations are in weight percentage relative to the total weight of the composition.

Composition 4
  Components and Concentrations
  First Composition
  a) 1.4 diamino butane and butylenyl-1,4 diphosphoric acid at a 1:2 molar ratio, 5 wt %;
  b) Isopropyl alcohol—20 wt %;
  c) n-butyl alcohol—20 wt %;
  d) Ethyl acetate—10 wt %;
  e) Copolymer of hydroxyethyl (meth)acrylate and methyl (meth)acrylate—10 wt %;
  f) Water—18 wt %;
  g) DMSO—2 wt %;
  Second Composition
  h) Cyclohexyl diisocyanate—2 wt %;
  i) Propyl acetate 13 wt %;
  Concentrations are in weight percentage relative to the total weight of the composition.
  The first composition is applied, allowed to rest on the nail plate for a time sufficient to enable penetration, then the second composition is applied to crosslink the copolymer by chemical reaction.

Composition 5
  a) 1,6 diamino hexane and maleic acid at a 1:2 molar ratio, 3 wt %;
  b) Ethanol—70 wt %;
  c) Ethyl acetate—20 wt %;
  d) DMSO—7 wt %.
  Concentrations are in weight percentage relative to the total weight of the composition.

Composition 6 (Projected Variations)
  a) Diamine alone such as butane-1,4-diamine, pentane-1,5-diamine or hexane-1,6-diamine;
  b) Alcohol such as ethanol, isopropanol or n-butanol;
  c) Optional water at a low weight percent;
  d) Film former selected from nitrocellulose, ethyl cellulose or cellulose acetate;
  e) Optional cross linker alone or in combination with film former—a copolymer of hydroxyethyl (meth)acrylate and methyl (met)acrylate with a second composition to be mixed with copolymer at time of use; cyclohexyl diisocyanate in propyl acetate;
  f) Optional cationic surfactant for leveling of coating for optional use with film former alone—behentrimonium or cetyl trimonium chloride;
  g) Optional stearyl or cetyl alcohol for use with cationic surfactant;
  h) DMSO Methods of Application The composition may be formulated as an immersion liquid or as a coatable gel. Compositions 1-4 concern a coatable gel. Composition 5 concerns an immersion liquid. Composition 6 is an example of a coatable gel using a diamine alone and may be combined with a cross-linker such as a diisocyanate. If a diisocyanate is added, the diamine and polymer with pendant hydroxyl groups may both combine with the diisocyanate.

The coatable gel of compositions 1-3 is mixed together and brushed onto a nail plate to form a gel coating of about one millimeter thick. The gel coating is maintained for a period sufficient to allow the complex to penetrate the surface of the plate, approximately 5 minutes to 30 minutes, preferably 5 minutes to about 10 minutes. The gel coating is then dried to evaporate the organic-water solvent.

If an activatable polymer is present as in composition 4, the first part of the composition is applied and allowed to stand on the nail plate for a time of approximately 5 minutes to 30 minutes, preferably about 5 minutes to 10 minutes. Then the second part of the composition is applied to the undried first part and allowed to cross link the copolymer of the first part. The heat from the cross linking will evaporate the solvent medium to leave a cured coating.

If an activatable polymer that is crosslinkable by actinic radiation is present, all components of the composition can be combined and the composition brushed onto the nail plate. The coating in a wet but statically stable state can rest on the nail plate for a period of approximately 5 minutes to 30 minutes, preferably about 5 minutes to 10 minutes. The coating is then partially dried with mild heat and subsequently or simultaneously irradiated with actinic radiation (UV light) to cause cross linking of the activatable polymer.

The immersion liquid of composition 5 is prepared by mixing all components at the designated concentrations and placing the composition into a container of appropriate dimension for immersion of fingers, toes or hooves.

Depending upon the selection of ingredients for composition 6, it may be a gel or a liquid and can be dried to form a coating when a cellulosic film former is present or it can be heated and/or irradiated if an appropriate cross-linker ingredient is present.

Examples

Nail Hardener Preparation and Application
Methods:
1. Baseline cow hoof samples preparation
Cut cow hooves into equal pieces size ~3 cm long×0.75 cm wide×2 mm thick. Collect pieces and keep at room temperature prior to testing.
3 groups of cow hooves, each one exposed to one solvent
Immerse sliced cow hoof samples in solvent (n-butanol, ethanol or dimethyl sulfoxide) for 24 hours in an air-tight glass container at room temperature.
Rinse cow hoof samples in DI water and Isopropanol, wash in ultrasonic water bath for 15 minutes.
Dry samples in vacuum chamber for 15 minutes. Pack samples in vacuum bag.
2. Crosslinker treated cow hoof samples preparation
Composition example 1, Prepare 1, 3, 5 and 7% by weight solutions of Hexamethylene diamine/Maleic acid, ratio 1:2, in ethanol—example of inventive composition.
Preparation 2, Prepare 1, 3 and 5% by weight solutions of formaldehyde in ethanol—standard for comparison.
Preparation 3, Prepare 1 and 3% by weight solutions of bismaleimidohexane (BMH) in dimethyl sulfoxide—example of covalent substance.
Preparation 4, Prepare 1, 1.7 and 2.3% by weight solutions of hexamethylene diamine in ethanol—diamine alone.
Preparation 5, Prepare 3.3% by weight solution of maleic acid in ethanol-maleic acid alone.
3. Application of composition example 1 and preparations 2-5 to cow hooves
5 groups of cow hooves, each one exposed to composition example 1 or preparations 2-5
Immerse cow hoof samples in solutions for 24 hours in an air-tight glass container at room temperature, one cow hoof per container filled with solution.
Rinse cow hoof samples in DI water and Isopropanol, wash in ultrasonic water bath for 15 minutes.
Dry samples in vacuum chamber for 15 minutes. Pack samples in vacuum bag.
4. Three-point bend test for untreated and treated cow hoof samples
Perform using a Texture Analyzer TAXT Plus from Texture Technologies.
Three point bend test is conducted until sample fracture.
Flexural strength is calculated based on force at break for each sample.

Results

A 3-point bend test set-up was used to measure the break force of treated and untreated cow hoof slices with thickness ranging from 0.88 mm to 2.75 mm. The flexural strength was calculated for each sample, based on sample thickness and width. For each group, the average flexural strength and the standard deviation were calculated. The p-value for the effect significance was calculated for each treated group versus the corresponding baseline value using ANOVA. Outliers were eliminated using the modified Thompson Tau method. Baseline values were determined for groups of untreated samples. Because the hypothesis is that the cross-linker reacts with thiol groups, the effect of dithiothreitol (DTT), a disulfide reducing agent, was tested as well. It was found that DTT has no significant effect on the flexural strength (results not shown).

Tested Solutions:
COMPOSITION example 1—hexamethylene diamine and maleic acid with a 1:2 ratio, concentrations (w/w): 1%, 3%, 5% and 7%; at 10%, strong precipitation was observed.
PREPARATION 2, Formaldehyde, concentrations (w/w): 1%, 3% and 5%.
PREPARATION 3, BMH, concentrations (w/w): 1% and 3%; at 3.5%, gelification was observed.
COMPOSITION 6, Hexamethylene diamine at 1% (w/w) (equal. to the 3% combination), 1.7% (w/w) (equal. to the 5% combination) and 2.3% (w/w) (equal. to the 7% combination).
PREPARATION 5, Maleic acid at 3.3% (w/w) (equal. to the 5% combination).
Results are displayed in tables 1, 2, 3, 4 and 5.

TABLE 1

| Hexamethylene diamine + Maleic acid | | | | | |
|---|---|---|---|---|---|
| % HMD + MA | N | FS (N/mm2) | stdev | p-value | % increase |
| 0 | 36 | 127 | 29 | N/A | N/A |
| 1 | 15 | 144 | 31 | 0.065 | 13.4 |
| 3 | 13 | 149 | 23 | 0.015 | 17.3 |
| 5 | 12 | 149 | 13 | 0.014 | 17.3 |
| 7 | 15 | 132 | 39 | 0.615 | 3.9 |
| 10 | Strong Polymerization | | | | |

TABLE 2

Formaldehyde

| % F | N | FS (N/mm2) | stdev | p-value | % increase |
|---|---|---|---|---|---|
| 0 | 21 | 117 | 30 | N/A | N/A |
| 1 | 10 | 141 | 25 | 0.040 | 20.5 |
| 3 | 13 | 132 | 31 | 0.198 | 12.8 |
| 5 | 20 | 134 | 28 | 0.068 | 14.5 |

TABLE 3

Bismaleimidohexane

| % B | N | FS (N/mm2) | stdev | p-value | % increase |
|---|---|---|---|---|---|
| 0 | 9 | 144 | 15 | N/A | N/A |
| 1 | 10 | 158 | 15 | 0.065 | 9.7 |
| 3 | 10 | 156 | 44 | 0.436 | 8.3 |
| 3.5 | | | | Gelification | |

TABLE 4

Hexamethylene diamine

| equal. % H + M | % H | N | FS (N/mm2) | stdev | p-value | % increase |
|---|---|---|---|---|---|---|
| 0 | 0 | 36 | 127 | 29 | N/A | N/A |
| 1 | — | — | — | — | — | — |
| 3 | 1 | 17 | 132 | 21 | 0.498 | 3.9 |
| 5 | 1.7 | 7 | 149 | 10 | 0.053 | 17.3 |
| 7 | 2.3 | 15 | 122 | 23 | 0.610 | -3.9 |

TABLE 5

Maleic Acid

| equ. % H + M | % M | N | FS (N/mm2) | stdev | p-value | % increase |
|---|---|---|---|---|---|---|
| 0 | 0 | 36 | 127 | 29 | N/A | N/A |
| 5 | 3.3 | 7 | 131 | 8 | 0.680 | 3.1 |

Conclusions

Example of composition embodiment of invention with hexamethylene diamine and maleic acid (1:2 ratio) at 3% and 5% (w/w) resulted in a significant increase in flexural strength. Formaldehyde at 1% results in a significant increase in flexural strength similar to the increase obtained for HMD+MA at 3% and 5%. There is a decrease in flexural strength for formaldehyde at 3% and 5%. There are indications that formaldehyde forms a "crust" on the surface of the samples at higher concentrations. This is also supported by the fact that formaldehyde is very reactive and bonds with the tissue surface, which prevents it from diffusing deeper. This translates into a few samples not breaking completely, leaving a "sliver" of material at the surface. On the contrary, HMD+MA penetrates deeper inside the tissue. By only taking into account the samples thinner than 1.8 mm, a greater increase in flexural strength was observed for both HMD and MA and formaldehyde, but this increase is more important for HMD+MA than for formaldehyde. Results are displayed in table 6.

TABLE 6

HMD + MA and formaldehyde samples thinner than 1.8 mm

| % HMD + MA | N | % Increase | p-value | % F | N | % Increase | p-value |
|---|---|---|---|---|---|---|---|
| All 1 | 15 | 13.4 | 0.065 | 1 | 10 | 20.5 | 0.040 |
| <1.8 mm 1 | 11 | 20.2 | 0.112 | 1 | 6 | 22.2 | 0.104 |
| All 3 | 13 | 17.3 | 0.015 | 3 | 13 | 12.8 | 0.198 |
| <1.8 mm 3 | 10 | 24.2 | 0.037 | 3 | 11 | 15.4 | 0.208 |
| All 5 | 29 | 17.3 | 0.014 | 5 | 20 | 14.5 | 0.068 |
| <1.8 mm 5 | 8 | 28.2 | 0.022 | 5 | 12 | 20.5 | 0.047 |

Bismaleimidohexane (BMH) at 1% and 3% results in a non-significant increase of the flexural strength, indicating there is most likely a small strengthening contribution from the actual reaction with thiol groups. HMD taken separately shows a borderline significant strengthening effect at 1.7%, while MA does not seem to have any significant effect. Maleic acid most likely contributes to strengthening when associated to hexamethylene diamine to form the HMD+MA complex and enables the reaction with thiols. It also has an effect in reducing yellowing due to the diamine.

Structures of tested examples are:

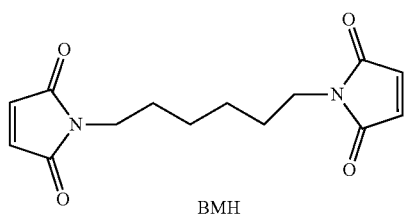

BMH
Bismaleimidohexane

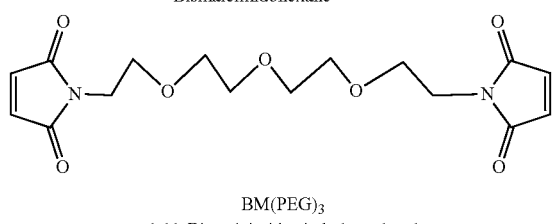

BM(PEG)$_3$
1.11-Bismaleimidotriethyleneglycol

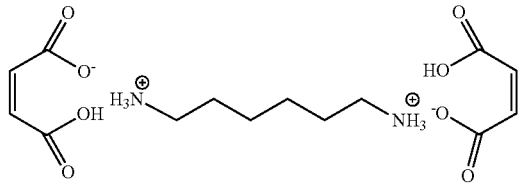

Complex
H$_2$N—(CH$_2$)$_6$-NH$_2$
1,6 hexane diamine
HOOC-CH=CH-COOH
Maleic Acid (cis configuration)

What is claimed is:

1. A composition for application to a nail or hoof plate comprising a mixture of an aqueous-organic medium, a diamine, and a rheologic agent to provide thixotropic property to composition, wherein:
   the diamine is an alkylenyl diamine of Formula I with n being 2 to 12:

H$_2$N-(CH$_2$)$_n$-NH$_2$   Formula I the diamine is the sole active agent at a concentration of from about 1 wt% to about 8 wt % relative to the total weight of the composition and the pH of the mixture is maintained at about 6 to about 8.

2. The composition according to claim 1 wherein the rheologic agent comprises a polyol, a polyether, a polyester, a poly(meth)acrylate, a cellulosic ether, a cellulosic ester or a combination thereof.

3. The composition according to claim 1 wherein the organic liquid of the aqueous organic medium comprises a mono, di or polyol, a ketone, a water-soluble terpenoid, DMSO or a combination thereof and the organic liquid is optionally also a penetration agent.

4. The composition according to claim 3 wherein the pH is managed by a buffer.

5. The composition according to claim 1 wherein the concentration of the diamine in the composition is from about 1 wt % to about 5 wt% relative to the total weight of the composition.

6. A composition for application to a nail or hoof plate comprising a mixture of an aqueous-organic medium and a non-covalent complex of a diamine and an organic acid, wherein:
the diamine is an alkylenyl diamine of Formula I with n being 2 to 12:
$H_2N\text{-}(CH_2)_n\text{-}NH_2$ Formula I and,
the organic acid is itaconic acid, acrylic acid, butenoic acid, pentenoic acid, maleic acid, fumaric acid, butenyl-1,4-dicarboxylic acid, hexenyl-1,6-dicarboxylic acid, pentenyl dicarboxylic acid or is an acid of Formula II:

$R^1\text{-}CY\text{-}Z\text{-}CH\text{-}R^2\text{-}X$  Formula II wherein:
Z is an unsaturated bond between CY and CH;
$R^1$ is phenyl or an alkyl group of one to four carbons;
$R^2$ is an alkylenyl group of the formula $-(CH_2)_m-$ wherein the designator m is zero or an integer of 1 to 4 such that $R^2$ is either absent or is present as a carbon chain;
Y and X are each independently hydrogen or a carboxylic, phosphoric or sulfonic acid group provided that at least one of X and Y is an acid group, and when X and Y are both carboxylic acid, or when the organic acid is maleic acid, fumaric acid, butenyl-1,4- dicarboxylic acid, hexenyl-1,6-dicarboxylic acid or pentenyl dicarboxylic acid, the organic acid is the dicarboxylic acid or the imide or anhydride form thereof.

7. The composition according to claim 6 further comprising a pH of about 6 to about 8.

8. The composition according to claim 6 further comprising a rheology agent.

9. The composition according to claim 8 wherein the rheology agent comprises a polyol, a polyether, a polyester, a poly(meth)acrylate, a cellulosic ether, a cellulosic ester or a combination thereof and the rheologic agent provides thixotropic gel character to the composition.

10. The composition according to claim 6 wherein the organic acid is (meth)acrylic acid, maleic acid, fumaric acid, butenoic acid, pentenoic acid, butenyl-1,4-dicarboxylic acid, pentenyl dicarboxylic acid, hexenyl-1,6-dicarboxylic acid or itaconic acid.

11. The composition according to claim 6 wherein the diamine and organic acid are present in the complex respectively at a molar ratio of about 1:1 to about 1:4.

12. The composition according to claim 6 wherein the concentration of the complex in the composition is from about 1 wt % to about 8 wt% or about 1 wt% to about 5 wt% relative to the total weight of the composition.

13. The A composition according to claim 1 further comprising a film former mono-polymer, copolymer or terpolymer comprising at least a (meth)acrylate polymer, a (meth)acrylate-vinyl copolymer, an ester polymer, an amide polymer, a vinyl or olefin polymer, a urethane polymer, a cellulosic polymer or a combination thereof; wherein:
the cellulosic polymer is nitrocellulose, ethyl cellulose, cellulose acetate butyrate, cellulose acetate phthalate, cellulose acetate trimellitate, hydroxypropyl methylcellulose, hydroxypropyl methylcellulose phthalate or any combination thereof;
the (meth)acrylate polymer is a polymer of one or more alkyl (meth)acrylate monomers alone or in combination with one or more additional olefin monomers wherein the additional olefin monomer comprises styrene, vinyl acetate, vinyl pyrrolidone, butene, butadiene, cyclopentene, cyclopentadiene or any combination thereof, and the (meth)acrylate polymer is optionally crosslinked with a di-olefin or with a diamine and the di-olefin comprises divinyl benzene, butadiene or $C_2$ to $C_6$ alkylenyl di(meth)acrylate;
the ester polymer is a polymer of lactide or glycolide; a polymer of a mixture of $C_2$ to $C_6$ hydroxyalkanoic acids; or a polymer of a $C_3$ to $C_6$ dicarboxylic acid and a $C_2$ to $C_6$ alkylenyl diol and the ester polymer is optionally crosslinked with a triol and/or a tri carboxylic acid; and
the vinyl polymer is polyvinyl alcohol, polyvinyl pyrrolidone, polystyrene, polyvinyl acetate, polyvinyl phthalate, polyvinyl benzoate, polyvinyl methoxide, polyvinyl butyral or any combination thereof.

14. The composition according to claim 6 further comprising a film former mono-polymer, copolymer or terpolymer comprising at least a (meth)acrylate polymer, a (meth)acrylate-vinyl copolymer, an ester polymer, an amide polymer, a vinyl or olefin polymer, a urethane polymer, a cellulosic polymer or a combination thereof; wherein:
the cellulosic polymer is nitrocellulose, ethyl cellulose, cellulose acetate butyrate, cellulose acetate phthalate, cellulose acetate trimellitate, hydroxypropyl methylcellulose, hydroxypropyl methylcellulose phthalate or any combination thereof;
the (meth)acrylate polymer is a polymer of one or more alkyl (meth)acrylate monomers alone or in combination with one or more additional olefin monomers wherein the additional olefin monomer comprises styrene, vinyl acetate, vinyl pyrrolidone, butene, butadiene, cyclopentene, cyclopentadiene or any combination thereof, and the (meth)acrylate polymer is optionally crosslinked with a di-olefin or with a diamine and the di-olefin comprises divinyl benzene, butadiene or $C_2$ to $C_6$ alkylenyl di(meth)acrylate;
the ester polymer is a polymer of lactide or glycolide; a polymer of a mixture of $C_2$ to $C_6$ hydroxyalkanoic acids; or a polymer of a $C_3$ to $C_6$ dicarboxylic acid and a $C_2$ to $C_6$ alkylenyl diol and the ester polymer is optionally crosslinked with a triol and/or a tri carboxylic acid; and
the vinyl polymer is polyvinyl alcohol, polyvinyl pyrrolidone, polystyrene, polyvinyl acetate, polyvinyl phthalate, polyvinyl benzoate, polyvinyl methoxide, polyvinyl butyral or any combination thereof.

15. The composition according to claim 13 wherein the composition further comprises one or more of a surfactant, a plasticizer, a fatty alcohol, coloring agent, a penetration agent, a perfume and/or a preservative.

16. The composition according to claim 14 wherein the composition further comprises one or more of a surfactant, a plasticizer, a fatty alcohol, coloring agent, a penetration agent, a perfume and/or a preservative.

17. The composition according to claim 1 wherein the total solids concentration in the composition is in the range of about 8 wt% to about 80 wt% relative to the total weight of the composition; or in the range of about 15 wt% to about 40 wt% relative to the total weight of the composition.

18. The composition according to claim 6 wherein the total solids concentration in the composition is in the range of about 8 wt% to about 80 wt% relative to the total weight of the composition; or in the range of about 15 wt% to about 40 wt% relative to the total weight of the composition.

19. A method comprising applying the composition of claim 1 to the nail plate by painting, brushing, dabbing or applying the composition onto the nail plate to form a gel coating and allowing the gel coating to remain in contact with the nail plate for a time of from about 1 minute to about 1 hour.

20. A method comprising applying the composition of claim 6 to the nail plate by painting, brushing, dabbing or applying the composition onto the nail plate to form a gel coating and allowing the gel coating to remain in contact with the nail plate for a time of from about 1 minute to about 1 hour.

21. The method according to claim 19 wherein the diamine is butane-1-4-diamine, pentane-1,5-diamine or hexane-1,6-diamine or any combination thereof; or the diamine is hexane-1,6-diamine.

22. The method according to claim 20 wherein the diamine is butane-1-4-diamine, pentane-1,5-diamine or hexane-1,6-diamine or any combination thereof; or the diamine is hexane-1,6-diamine.

23. The method according to claim 19 wherein a weak, brittle, inflexible, cracked and/or broken nail or hoof is at least partially hardened and/or healed.

24. The method according to claim 20 wherein a weak, brittle, inflexible, cracked and/or broken nail or hoof is at least partially hardened and/or healed.

25. The composition according to claim 10 wherein the organic acid is maleic acid, fumaric acid, itaconic acid or (meth)acrylic acid.

* * * * *